United States Patent [19]

Hempton

[11] Patent Number: 5,035,761
[45] Date of Patent: Jul. 30, 1991

[54] METHOD FOR CROSS-SECTIONING YARN SAMPLES

[75] Inventor: Robert F. Hempton, Wilmington, Del.

[73] Assignee: E. I. du Pont de Nemours and Company, Wilmington, Del.

[21] Appl. No.: 443,372

[22] Filed: Nov. 30, 1989

[51] Int. Cl.$^5$ .............................................. B32B 31/00
[52] U.S. Cl. .................................. 156/161; 156/160; 156/250; 83/915.5; 73/160; 264/229; 264/231; 264/158; 269/287; 269/288
[58] Field of Search .............. 156/161, 160, 165, 250, 156/166, 229; 83/915.5; 73/160; 264/229, 231, 158; 269/288, 287

[56] References Cited

U.S. PATENT DOCUMENTS

| | | | |
|---|---|---|---|
| 1,940,590 | 12/1933 | Hardy | 83/915.5 |
| 2,011,444 | 8/1935 | Hardy | 83/915.5 |
| 2,048,335 | 7/1936 | Hardy | 83/915.5 |
| 4,233,363 | 11/1980 | Cenel et al. | |
| 4,364,998 | 12/1982 | Wei | |
| 4,790,132 | 12/1988 | Nelson | |

OTHER PUBLICATIONS

American Dyestuff Reporter, Olsen, Mar. 1972, pp. 58, 60, and 62.
de Gruy, Ines V., "Fabric Embedding for Microtome Sectioning," *Textile Research Journal*, vol. 25, No. 10, Oct. 1955.

Primary Examiner—Michael W. Ball
Assistant Examiner—Jeff H. Aftergut

[57] ABSTRACT

A method for preparing cross-sections of yarn samples along the plane perpendicular to the yarn's longitudinal axis is disclosed. This method involves the steps of passing the yarn through a hollow capsule so that the axes of the yarn and the capsule are aligned in parallel, tensioning the yarn to remove any crimp, forming a solid stub inside the capsule to fix the position of the tensioned yarn, and then cross-sectioning the stub perpendicular to its longitudinal axis.

4 Claims, 1 Drawing Sheet

METHOD FOR CROSS-SECTIONING YARN SAMPLES

This invention pertains to a method for preparing embedded yarn specimens for microscopic analysis of fiber cross-sections. More specifically, the method involves embedding a decrimped yarn having one or more filaments in a cureable liquid in a sample container such that the filaments' longitudinal axes are aligned parallel to the longitudinal axis of the container. Cross-sectioning of the embedded yarn specimen perpendicular to the fibers' axes to obtain true filament cross-sections for microscopic analysis is readily achieved.

BACKGROUND OF THE INVENTION

A number of methods for preparing specimens for microscopic analysis of fiber cross-sections are known. Olson, et al., *American Dyestuff Reporter*, March 1972, p. 58, describes a method in which a crimped yarn is mounted on a frame under tension sufficient to remove the yarn crimp, and the frame is placed into a capsule with a cureable resin to obtain an embedded yarn sample for cross-sectioning with a microtome. Cemel, et al., U.S. Pat. No. 4,233,363 discloses a procedure whereby a crimped yarn is mounted on a frame under tension and the samples dipped into a lacquer to freeze the filaments in their relative positions. The sample is then cut and mounted in a holder. Nelson, U.S. Pat. No. 4,790,132 describes a method whereby a crimped yarn is hung on a rack hook and sufficient weight is added to the yarn to pull out the crimp. Acrylic lacquer is applied dropwise to the yarn, the sample is allowed to dry and is placed in a mold cavity where it is embedded in epoxy. None of these methods discloses a means for aligning the decrimped yarn sample within the sample holder during the embedding process.

Synthetic fibers are produced having a wide range of cross-sections in order to achieve specific physical effects such as hand, luster, and soil-hiding in substrates made from the yarns. In many instances, in order to characterize a yarn sample, it is desirable to obtain a true cross-section of the filaments which make up the yarn bundle so that a microscopic analysis of the cross-section can then be made. By true cross-section, it is meant the cross-section taken at right angles to the longitudinal axis of a filament. In a multifilament crimped yarn, all of the filaments must be decrimped and approximately aligned in a parallel orientation within the yarn bundle in order to cross-section the sample perpendicular to all of the filaments in the yarn bundle.

The above-mentioned methods provide means for decrimping and aligning filaments within a yarn sample prior to embedding in a resin in a sample container, but the orientation of the decrimped yarn bundle in the sample container is not controlled If the yarn bundle is not aligned parallel to the axis of the hardened resinous stub, it is necessary to align the yarn bundle which is embedded in the resinous specimen perpendicular to the microtome blade. Such alignment may be difficult to effect accurately because the end of the stub is often facetted by trimming prior to sectioning, making viewing of the yarn bundle difficult. Difficulties in viewing the embedded yarn bundle also can arise due to opacity of the embedding resin used.

SUMMARY OF THE INVENTION

The current invention is directed to a method for cross-sectioning a yarn of one or more filaments along the plane perpendicular to the yarn's longitudinal axis. This method comprises the steps of:

(a) passing one end of the yarn through a hollow capsule so that the filaments are in substantially parallel alignment with the longitudinal axis of the capsule;

(b) tensioning the yarn to straighten the filaments and substantially remove any crimp;

(c) forming a solid mass inside the capsule to fix the position of the tensioned yarn; and (d) cross-sectioning the solid mass perpendicular to its longitudinal axis.

In a preferred embodiment the mass-forming step is performed by introducing a cureable embedding resin into the capsule and subsequently curing the resin to fix the position of the filaments within a solid mass in the form of a hardened, resinous stub. The preferred means for performing the cross-sectioning step is with a microtome.

DETAILED DESCRIPTION

A yarn sample is tied to a support arranged such that the yarn can hang freely. The yarn sample is threaded through a hole formed in the bottom of a specimen capsule so that the capsule is positioned upright on the yarn. A variety of capsules for preparation of specimens for microtoming are commercially available. It is preferable that the capsule be pointed on at least one end with the point approximately centered with the central axis of the capsule. This serves to facilitate alignment of the yarn sample with the capsule axis by forming a hole at the end of the point at the bottom of the capsule and a corresponding hole in the center of the lid of the capsule. The hole should be approximately the size of the diameter of the yarn bundle while it is being tensioned. If the hole is too large, the yarn will not be restricted to be aligned with the axis of the capsule, resulting in slight misalignment.

Straightening of the yarn is readily effected by attaching a weight to the free end. The weight must be sufficient to align and straighten the filaments within the yarn and to remove any crimp from the yarn but not so great as to stretch the fibers within the yarn which will result in a distortion of the as-produced fiber cross-section. The amount of weight needed to straighten a crimped or uncrimped yarn is approximately 0.03–0.06 g/denier (0.3–0.5 g/tex), as described in ASTM D1577. In some instances more weight, 0.1 g/denier (0.9 g/tex) or higher may be required. For nylon fibers, up to 0.1–0.8 g/denier (0.9–7.2 g/tex) may typically be used without cold-drawing the filaments.

In order to prevent leakage of the embedding resin out of the hole in the bottom of the capsule, the hole is sealed using tape or other sealing means. A glue or resin may be used to seal the hole, however this requires additional time for hardening of the seal. A suitable embedding resin is introduced through the top of the capsule. A wide variety of commercially available epoxy resins or wax may be used. A slit is made using a razor blade or other cutting means from one edge of the capsule lid to the hole in the center. The yarn is inserted through the slit and centered in the hole in the lid and the lid is put in place on top of the capsule. Alternately, the yarn can be threaded through the hole in the capsule lid prior to threading through the hole in the capsule bottom at the beginning of the procedure. The holes in the top and bottom of the capsule serve to align the yarn with the central axis of the capsule when the lid is in place. It is only necessary that the yarn bundle is aligned parallel with the capsule axis; it need not be centered in the capsule. However, using the center points of the capsule lid and bottom greatly facilitates the alignment process.

Figure 1:
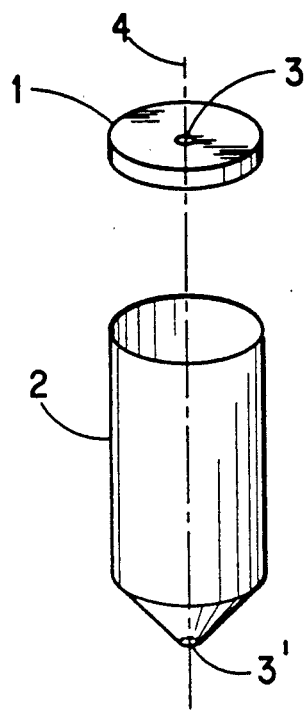
FIG. 1 depicts a hollow capsule and capsule lid of a type suitable for use with this invention.
Figure 2:
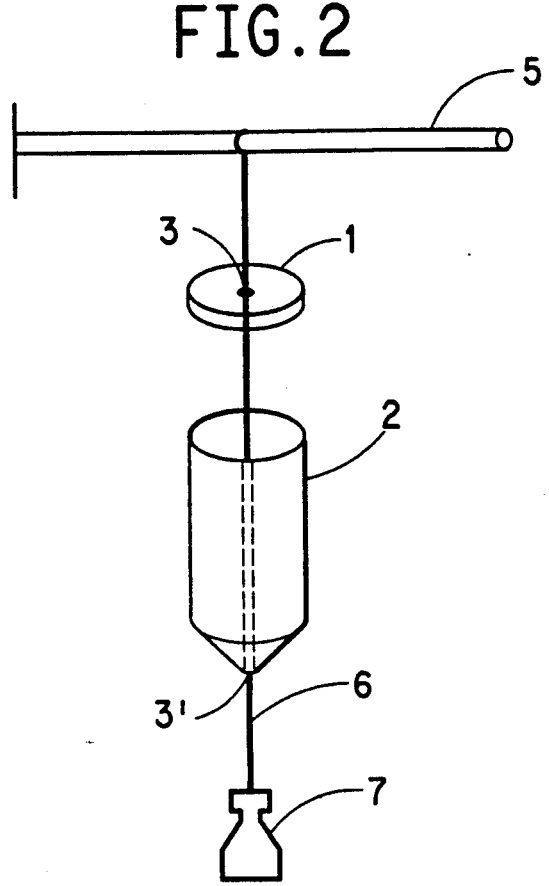
FIG. 2 shows a tensioned yarn having been passed through a hollow capsule so that the filaments of the yarn are aligned parallel to the longitudinal axis of the capsule.

Referring to FIGS. 1-2, a yarn sample 6 is tied to a support 5 arranged such that it can hang freely. Holes 3 and 3' are formed in both the center of a capsule bottom 2 and its lid 1 such that when the lid is placed on the capsule the two holes line up along the capsule axis 4. The yarn is threaded through both the capsule lid and bottom such that the capsule is in an upright position on the yarn as shown in FIG. 2. Hole 3' is sealed using tape, glue, or other sealing means. A suitable embedding resin is introduced through the top of the capsule and the lid put in place on the top of the capsule, thus aligning the yarn axis parallel to the capsule axis 4. Alternately, the capsule lid may be threaded onto the yarn after introducing the resin into the capsule by making a slit from the edge of the lid to the central hole and sliding the yarn through the slit until it is centered in the hole. Once the resin is cured, the resinous or wax stub containing the aligned yarn sample is removed from the capsule, any excess yarn extending from the ends of the solid mass is trimmed off, and the stub is prepared for microtoming using standard techniques.

Figure 3:
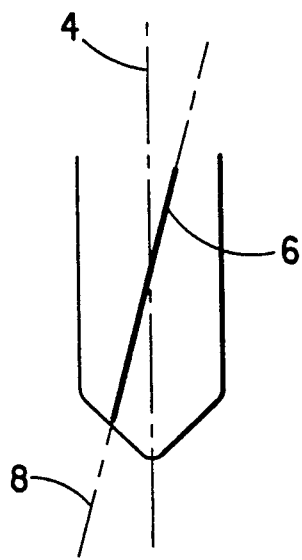
FIG. 3 is a close-up of a yarn which is not aligned parallel to the longitudinal axis of the capsule and which would consequently be difficult to cross-section along a plane perpendicular to the yarn's longitudinal axis.

Microtoming perpendicular to the yarn axis is accomplished by adjusting the microtome blade perpendicular to the stub axis. Because the yarn is aligned parallel to the stub axis, a true cross-section is obtained using this method. Methods disclosed in the prior art remove the crimp from the yarn sample but they do not provide a means for accurately aligning the yarn sample parallel to the capsule axis. FIG. 3 shows a yarn sample which has been mounted off-axis In order to adjust the microtome blade perpendicular to the yarn axis 8 to obtain a true cross-section, it is necessary to visually determine the position of the yarn in the stub which is difficult to do accurately due to the opacity of some resins and the fact that the yarn must be viewed through facetted surfaces of the resinous stub created during trimming of the sample which is commonly done prior to microtome sectioning.

Using this method, the hardened stub itself is aligned with its axis perpendicular to the microtome blade. Since the filaments are aligned parallel to the axis of the stub, they will be sectioned at right angles to the filaments' axes. Commercially available microtomes are designed such that the stub may be aligned with its axis perpendicular to the knife edge by a person having relatively little experience operating microtome apparatus. Once the microtome settings are selected such that a sample is aligned as described above, additional samples may be sectioned without further adjustment. This procedure is much simpler than aligning a yarn sample which is not aligned with the specimen axis, which has the problems mentioned above and requires a higher level of expertise on the part of the microtome operator. The method of this invention also eliminates the intermediate step of freezing the yarn in a straightened and decrimped configuration prior to embedding, resulting in a decrease in sample preparation time.

EXAMPLE

One end of a bulked continuous filament nylon 6,6 yarn (80 filaments, 1405 total denier, 4.5 modification ratio) was tied to a horizontal stainless steel rod. A small hole was introduced through the bottom of a "BEEM" embedding capsule (size 00) using a pointed metal forceps. A knot was tied in the free end of the yarn for ease in threading through the hole in the capsule. The free end of the yarn was threaded through the hole in the capsule bottom and a 200 gm weight was tied to this end to remove the yarn crimp. A piece of masking tape was wrapped around the bottom of the capsule and pinched around the yarn in order to provide a seal to prevent the resin from leaking out of the capsule. An epoxy resin was prepared by mixing the following: Marglas Resin 658 crystal-clear epoxy casting resin, 3 parts by volume; Marglas Resin 659, crystal-clear epoxy casting resin, 1 part by volume; and Maraset modified diamine curing agent Hardener 558, 2 parts by volume (manufacturer Acme Division, Allied Products Corporation). The resin was placed in a vacuum oven at 60° C. and a vacuum of approximately 20-25 inches of Hg (68-85 kPa) for 5 minutes to remove any bubbles and then was poured into the capsule. The capsule lid, having a hole in the center so as to line up with the hole in the capsule bottom, was slid onto the yarn through a slit cut from the edge of the capsule to the central hole. The lid was then placed securely on top of the capsule, thereby aligning the yarn along the central axis of the capsule. The yarn was left hanging approximately 12 hours at room temperature with the weight attached until the resin is cured. Alternately, the yarn may be hung inside an oven at 60° C. for 1 hour to cure the resin. The specimen stub was removed from the capsule, excess yarn trimmed from the ends, and trimmed for sectioning on a microtome. The stub was aligned in the microtome at right angles to the blade, and cross-sections having a thickness of 8 microns were prepared according to standard procedures well known in the art.

I claim:

1. A method for cross-sectioning a yarn of one or more filaments perpendicular to the yarn's longitudinal axis using a lidded embedding capsule having a longitudinal axis, two ends, and a hollow cavity between the ends, the lid being at one end of the capsule and having a hole therein of a diameter corresponding to the diameter of the yarn to be sectioned, said method comprising the steps of:

(a) making a hole in the end of the capsule opposite the lid, said hole forming an axis with the hole in the lid in substantially parallel alignment with the axis of the capsule;

(b) passing one end of the yarn through the hole in the lid, the hollow cavity, and the hole in the opposite end so that the one or more filaments are in substantially parallel alignment with the longitudinal axis of the capsule;

(c) tensioning the yarn to straighten and position the one or more filaments and substantially remove any crimp;

(d) forming a solid mass having a longitudinal axis inside the capsule to fix the position of the tensioned yarn; and (e) cross-sectioning the solid mass perpendicular to its longitudinal axis.

2. The method of claim 1 wherein the mass-forming step is performed by introducing an embedding resin into the capsule and subsequently curing the resin.

3. The method of claim 1 wherein the cross-sectioning step is performed using a microtome.

4. The method of claim 2 wherein the cross-sectioning step is performed using a microtome.

* * * * *